(12) United States Patent
Pire

(10) Patent No.: US 9,162,757 B2
(45) Date of Patent: Oct. 20, 2015

(54) TECHNICAL METHOD, A MAINTENANCE DEVICE, AND AN AIRCRAFT

(75) Inventor: Richard Pire, Istres (FR)

(73) Assignee: Airbus Helicopters, Marignane Cedex (FR)

( * ) Notice: Subject to any disclaimer, the term of this patent is extended or adjusted under 35 U.S.C. 154(b) by 696 days.

(21) Appl. No.: 13/484,658

(22) Filed: May 31, 2012

(65) Prior Publication Data

US 2012/0316832 A1 Dec. 13, 2012

(30) Foreign Application Priority Data

Jun. 7, 2011 (FR) .................................. 11 01725

(51) Int. Cl.
*G07C 5/08* (2006.01)
*G06F 11/30* (2006.01)
(Continued)

(52) U.S. Cl.
CPC ............... *B64C 27/001* (2013.01); *C07C 5/08* (2013.01); *G01M 7/00* (2013.01); *B64C 2027/004* (2013.01); *B64D 2045/0085* (2013.01); *G06F 11/30* (2013.01); *G06F 17/40* (2013.01); *G06F 19/00* (2013.01)

(58) Field of Classification Search
CPC ........ B60R 16/00; B60R 16/02; B60R 99/00; B60S 5/00; B64C 27/00; B64C 27/004; B64D 45/00; B64D 45/0085; B64D 47/00; B64D 47/02; G01D 7/00; G01D 9/00; G01D 21/00; G06F 11/00; G06F 11/30; G06F 11/3055; G06F 11/32; G06F 11/321; G06F 11/324; G06F 11/34; G06F 15/00; G06F 15/16; G06F 17/00; G06F 17/10; G06F 17/40; G06F 19/00; G07C 5/00; G07C 5/006; G07C 5/08; G07C 5/0808; G07C 11/00

USPC .................. 73/432.1, 570, 577, 865.8, 865.9, 73/866.3; 340/500, 540, 679, 683; 377/1, 377/16; 702/1, 33, 34, 127, 176, 178, 182, 702/187, 189; 708/100, 105, 200
See application file for complete search history.

(56) References Cited

U.S. PATENT DOCUMENTS 2,883,255 A * 4/1959 Anderson .................... 346/34
3,362,217 A * 1/1968 Rush et al. ................ 73/112.01

FOREIGN PATENT DOCUMENTS

EP 0541277 A2 5/1993

OTHER PUBLICATIONS

Airframe loads & usage monitoring of the CH-47D "Chinook" helicopter of the Royal Netherlands Air Force. Jun. 3, 2011 (Jun. 6, 2011). URL: http://www.nl.nl/?id=171881&l=en.
(Continued)

*Primary Examiner* — Edward Cosimano
(74) *Attorney, Agent, or Firm* — Brooks Kushman P.C.

(57) ABSTRACT

The present invention relates to a maintenance method for a piece of equipment (2) of a vehicle (1) including an anti-vibration system (3). In the method, a device (10) determines a first number (D1) of hours of operation of said equipment (2) while said anti-vibration system (3) was operating in a normal mode of operation and a second number (D2) of hours of operation while said anti-vibration system (3) was operating in a degraded mode of operation. Said second number (D2) is then converted into a third number (D3) by applying a predetermined conversion relationship. Under such circumstances, action is taken on said equipment (2) when the sum of the first number (D1) plus the third number (D3) reaches a predetermined threshold (D0).

7 Claims, 2 Drawing Sheets

(51) Int. Cl.
  *G06F 17/40* (2006.01)
  *G06F 19/00* (2011.01)
  *B64C 27/00* (2006.01)
  *C07C 5/08* (2006.01)
  *G01M 7/00* (2006.01)
  *B64D 45/00* (2006.01)

(56) References Cited

OTHER PUBLICATIONS

Search Report and Written Opinion; Application No. FR 1101725; dated Jan. 18, 2012.

\* cited by examiner

TECHNICAL METHOD, A MAINTENANCE DEVICE, AND AN AIRCRAFT

CROSS REFERENCE TO RELATED APPLICATIONS

The present application claims priority to FR 11 01725 filed on Jun. 7, 2011, the disclosure of which is incorporated in its entirety by reference herein.

BACKGROUND OF THE INVENTION (1) Field of the Invention

The invention relates to a technical method and to a maintenance device for a piece of equipment of a vehicle, and more particularly of an aircraft.

The invention is thus situated in particular in the technical field of on-board maintenance systems, and more specifically maintenance systems for electronic equipment.

(2) Background Art

Conventionally, a manufacturer specifies the lifetime of a piece of equipment, and may then perform tests in order to demonstrate that the lifetime of that equipment meets requirements. For example, the lifetime may be evaluated as a number of flying hours, e.g. 10,000 hours for a rotorcraft.

The equipment of an aircraft is subjected to non-negligible levels of vibration that might cause it to deteriorate. It is therefore appropriate to verify that the vibration is not of a kind that is likely to reduce the lifetime of the equipment. Under such circumstances, vibratory testing is performed on the equipment.

Nevertheless, it will be understood that it is difficult to perform tests for the complete lifetime of the equipment, since a test lasting for 10,000 hours, for example, is difficult to envisage at reasonable cost.

Consequently, the equipment is subjected to a vibratory spectrum greater than the vibratory spectrum to which the equipment is subjected in use, but for a duration that is shorter than the predicted lifetime for the equipment.

During a definition stage, a piece of equipment may be thus be subjected to an accelerated and destructive vibration test representing the stresses applied to the equipment during its specified lifetime.

The vibratory spectrum applied during such a test and the duration of the test are obtained by conventional methods, e.g. associating a duration with a vibratory level.

Furthermore, a vehicle, and in particular an aircraft, may be provided with active and passive anti-vibration systems. The vibratory spectrum to which a piece of equipment is subjected is thus determined by taking into consideration the use of such anti-vibration systems.

These anti-vibration systems are designed to present a very high level of reliability. Nevertheless, failure is not impossible, even if extremely rare.

Consequently, in the event of a failure of an anti-vibration system, a piece of equipment may be subjected to non-standard levels of vibration. The damage to the equipment may be increased significantly, e.g. by a factor of ten.

However, such levels of vibration are not always taken into consideration during the equipment definition stage, because of their improbability. Thus, when the vibratory level to which the equipment is subjected becomes increased over a non-negligible length of time, that gives rise to a decrease in the potential lifetime of the equipment.

It can be understood that this gives rise to a problem about the lifetime of pieces of equipment subjected to undue levels of vibratory stress, and to how to perform predictive maintenance on the equipment.

Systems are known that are based on "sentinels" that act in real time to measure the vibratory levels of pieces of equipment, and in particular of electronic cards. Those systems act in real time to measure the vibration to which a piece of equipment has been subjected and to deduce therefrom the remaining lifetime for that equipment.

Such systems are most advantageous, but they present cost that is not negligible.

Thus, document EP 0 541 277 describes an integrated vibration-reducing and structural health monitoring system. Maintenance tools with maintenance actions for performing on equipment as a function of its deterioration are provided, e.g. for a helicopter. Vibration reduction makes use of determining operation under a normal mode or a degraded mode.

Document XP 55016804 entitled, "Airframe loads & usage monitoring of the CH-47D 'Chinook' helicopter of the Royal Netherlands Air Force," A. Oldersma et al., published by the National Aerospace Laboratory, (Jun. 2011), describes working loads on structural frames and verification practices in a helicopter. Flying regimes are recognized in order to adjust how the actual wear of components is determined. Relative component operating durations are provided depending on speeds and various operating situations to which fatigue damage rates are associated.

These relative durations refer to percentages of a lifetime.

BRIEF SUMMARY OF THE INVENTION

An object of the present invention is thus to propose an alternative method at low cost for organizing the maintenance of a piece of equipment.

In an implementation of the invention, a technical maintenance method for a piece of equipment of a vehicle that includes an anti-vibration system, is remarkable in particular for the following steps:
- determining whether the anti-vibration system is operating in a normal mode of operation or in a degraded mode of operation;
- determining a first number of hours of operation of the equipment while the anti-vibration system was operating in the normal mode of operation;
- determining a second number of hours of operation of the equipment while the anti-vibration system was operating in the degraded mode of operation;
- converting the second number of hours of operation into a third number of hours of operation by applying a predetermined conversion relationship, the third number of hours of operation acting under normal operating mode conditions to generate damage to the equipment that is equal to the damage caused by the equipment operating during the second number of hours of operation; and
- acting on the equipment when the sum of the first number plus the third number reaches a predetermined threshold.

It should be observed that the term "anti-vibration system" is used to designate means for reducing vibration, and in particular vibration of the structure of the aircraft. In a rotorcraft, the anti-vibration system may involve means arranged on a lift rotor of the rotorcraft, or indeed on a main gearbox driving the lift rotor, for example.

Furthermore, the term "hours of operation" relates to the time spent by a piece of equipment on board a vehicle in operation, i.e. from the moment when the pilot acts on the vehicle to start its engine to the moment when a pilot stops the vehicle. This time is not equivalent to a percentage of a lifetime.

Thus, in the invention, during the definition stage, a manufacturer determines a predetermined threshold corresponding to a predicted lifetime of a piece of equipment and then determines a vibratory spectrum to which the equipment is subjected during that lifetime. The vibratory spectrum is referred to as the "estimated vibratory spectrum" for convenience.

The manufacturer verifies that the equipment is in compliance by performing an accelerated test that simulates the operation of the equipment during its lifetime with the estimated vibratory spectrum.

In use, in particular in flight in a vehicle of the aircraft type, a first number of hours of operation under normal conditions is then determined, i.e. conditions in which the anti-vibration system is operating in its normal operation mode.

Similarly, the operating duration of the equipment is also measured while the anti-vibration system is malfunctioning. Thus, when the anti-vibration system is operating in a degraded mode of operation, a second number of hours of operation is determined for said equipment.

Thereafter, using a conversion relationship that has been predetermined by the manufacturer, this second number of hours of operation is converted into a third number of hours of operation. For example, it may be established that one hour of operation during the degraded mode of operation is equivalent to ten hours of operation during the normal mode of operation in terms of damage to the equipment.

It should be observed that the term "relationship" designates any means providing information that enables the required conversion to be performed, e.g., for example: a mathematical relationship, a database, charts, or equivalent means.

Finally, action is taken on the equipment when the sum of the first number plus the third number reaches a predetermined threshold, i.e. the lifetime, for example. This step consists in a technical action performed on the equipment to remove it and then subject it to maintenance action seeking to extend its utilization, or else to replace it.

The method therefore does not require expensive dedicated means to be used. It thus resolves the technical problem posed of combating the effects of excessive and rare vibration on the equipment.

The invention may also include one or more of the following characteristics.

For example, the predetermined threshold may be equal to the predetermined lifetime of the equipment.

In another aspect, said anti-vibration system operates in the degraded mode of operation when said anti-vibration system has failed, at least in part.

In addition, said anti-vibration system is optionally an active device.

Furthermore, in order to determine said conversion relationship, the following steps are performed:
estimating the vibratory spectrum of said equipment in use while said anti-vibration system is operating in degraded mode, and deducing a mean vibration level therefrom;
determining an alternative threshold associated with said mean vibration level; and
deducing therefrom a conversion relationship corresponding to a multiplicative coefficient equal to the quotient of the predetermined threshold divided by the alternative threshold.

In addition to a method, the invention provides a device for maintaining a piece of equipment of a vehicle that includes an anti-vibration system.

The device is remarkable in particular in that it comprises a peripheral member and a processor unit communicating with the anti-vibration system, the processor unit being provided with a memory, the processor unit executing instructions stored in the memory in order to implement the method as explained above in particular to:
determine whether the anti-vibration system is operating in a normal mode of operation or in a degraded mode of operation;
determine a first number of hours of operation of the equipment while the anti-vibration system was operating in the normal mode of operation;
determine a second number of hours of operation of the equipment while the anti-vibration system was operating in the degraded mode of operation;
convert the second number of hours of operation into a third number of hours of operation by applying a predetermined conversion relationship; and
signal to an operator the sum of the first number of hours of operation plus the third number of hours of operation.

Finally, the invention provides an aircraft provided with the device.

BRIEF DESCRIPTION OF THE SEVERAL VIEWS OF THE DRAWINGS

The invention and its advantages appear in greater detail from the following description of embodiments given by way of illustration and with reference to the following figures, in which.

DETAILED DESCRIPTION OF THE INVENTION

Figure 1:
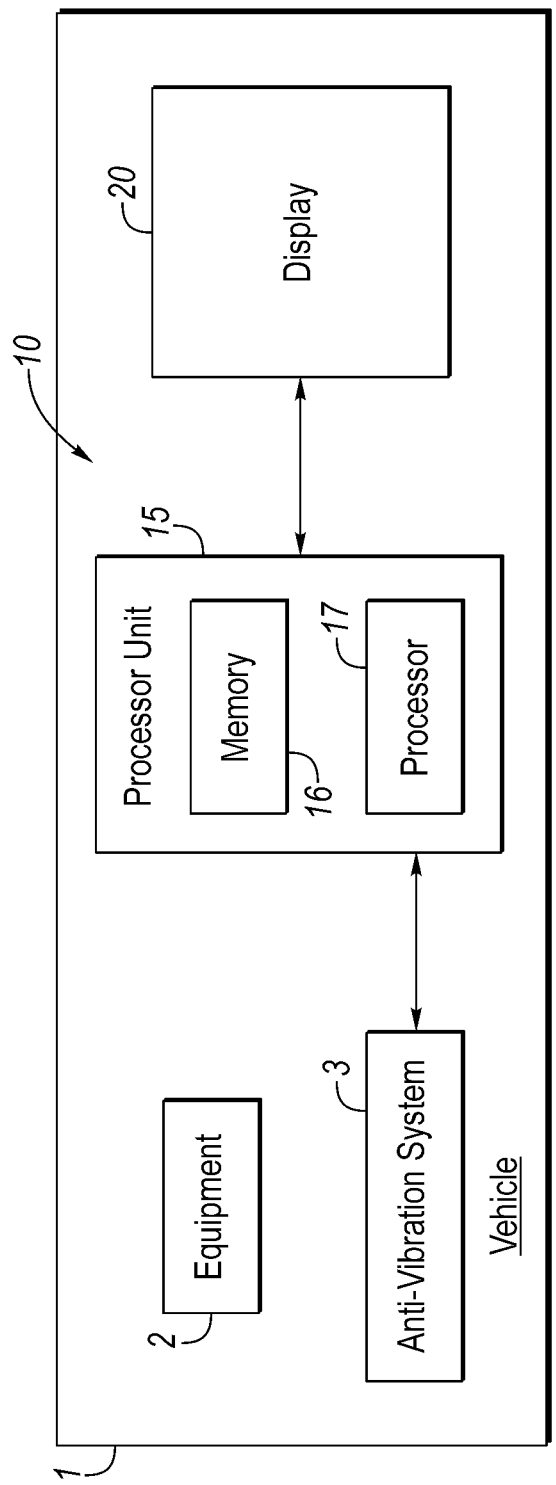
FIG. 1 is a diagram of a vehicle of the invention.

FIG. 1 shows a vehicle 1 of the invention, and more particularly aircraft.

It should be observed that the vehicle is shown diagrammatically to avoid pointlessly overcrowding FIG. 1.

The vehicle 1 includes at least one piece of equipment 2 such as an on-board electronic navigation chart. Furthermore, the vehicle 1 is provided with an anti-vibration system 3 for the purpose of at least reducing the vibration of a carrier structure of the vehicle, which anti-vibration system may be an active device.

The vehicle 1 also has a device 10 for maintaining the equipment 2.

The device 10 includes a processor unit 15 communicating with the anti-vibration system 3 so as to receive a discrete failure signal, where appropriate. Furthermore, the device 10 includes a peripheral member 20 communicating with the processor unit 15, the peripheral member possibly being a display screen or any other meaans for signaling information.

Under such circumstances, the processor unit 15 possesses a memory 16 and possibly at least one processor 17, the processor executing instructions stored in the memory 16 in order to inform an operator that action needs to be taken on the equipment. For example, the processor unit may cause a maintenance order to be displayed on the peripheral member 20.

Figure 2:
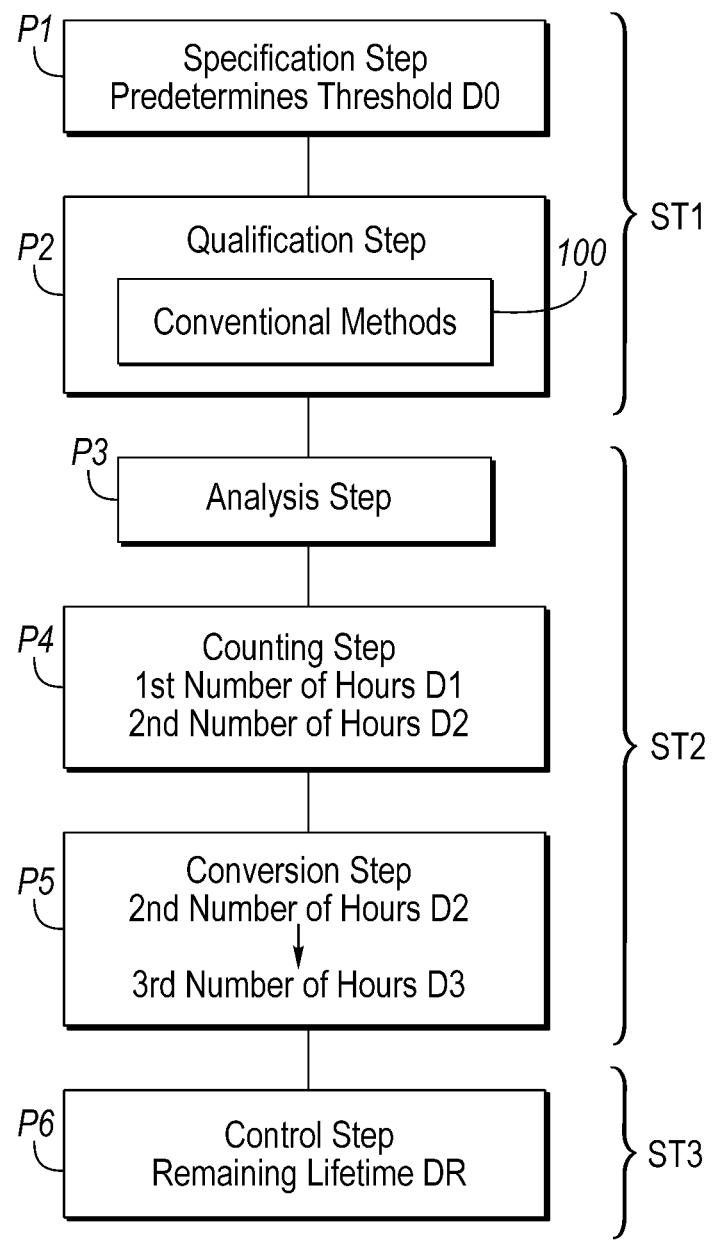
FIG. 2 is a diagram explaining a method of the invention.

FIG. 2 shows in particular how the automatic method is implemented by the device 10.

During a definition stage ST1, in a specification step P1, the vehicle manufacturer specifies a predetermined threshold D0 from which an operator needs to act on a piece of equipment 2.

For example, the predetermined threshold D0 may be a predicted lifetime that the equipment 2 ought to reach under normal operating conditions, i.e. ignoring associated failures.

During a qualification step P2, the manufacturer verifies that the equipment 2 satisfies requirements, and for example presents the predicted lifetime.

Using conventional methods 100, the manufacturer performs an accelerated vibration test by subjecting the equipment 2 to a level of vibration greater than the level of vibration to which the equipment 2 will be subjected during operation of the vehicle. Furthermore, the vibration test is performed for a duration that is shorter than the predetermined threshold, i.e. the predicted lifetime.

During an inventory-taking stage ST2 performed on board a vehicle, in an analysis step P3, the processor unit determines whether the anti-vibration system 3 is operating in a normal mode of operation or in a degraded mode of operation.

For example, the anti-vibration system 3 sends a discrete failure signal to the processor unit 15 during the degraded mode of operation. Reference may be made to the literature to obtain information about such signaling of a degraded mode of operation.

It should be observed that it may be considered that the anti-vibration system is operating in the degraded mode of operation when it has failed completely or only in part.

During a counting step P4, the processor unit 15 determines:
- a first number D1 of hours of operation of the equipment 2 while the anti-vibration system 3 was functioning in the normal mode of operation; and
- a second number D2 of hours of operation of the equipment 2 while the anti-vibration system 3 was functioning in the degraded mode of operation.

Furthermore, during a conversion step P5, the processor unit 15 determines a third number D3 of hours of operation by converting the second number D2 of hours of operation using a predetermined conversion relationship.

It should be observed that using the equipment during the third number D3 of hours of operation under normal operating mode conditions gives rise to damage to the equipment 2 that is equal to the damage that would be caused by operating the equipment 2 during the second number of hours of operation under degraded operating mode conditions.

In order to determine the conversion relationship, it is possible during the definition stage ST1 to simulate the vibratory spectrum of the equipment 2 in use while the anti-vibration system 3 is operating in degraded mode in order to deduce a mean level of vibration therefrom.

Under such circumstances, e.g. with the help of the relationship used during step P2, it is possible to determine an alternative threshold associated with said mean vibration level, and to deduce therefrom a conversion relationship corresponding to a multiplicative coefficient equal to the quotient of the predetermined threshold D0 divided by the alternative threshold.

During a control step P6 in a controlled stage ST3, the processor unit 15 determines whether the sum of the first number D1 of hours of operation plus the third number D3 of hours of operation has reached the predetermined threshold D0, and orders an operator to act on said equipment 2, where appropriate.

For example, the processor unit determines a remaining lifetime DR equal to the predicted lifetime D0 minus the sum of the first number D1 plus the second third number D3, i.e.:

$$DR = D0 - (D1 + D3).$$

If the remaining lifetime reaches zero, the operator is informed via the peripheral member 20. The operator may then revise the equipment 2, or may indeed replace it, for example.

Naturally, the present invention may be subjected to numerous variations as to its implementation. Although several implementations are described, it will readily be understood that it is not conceivable to identify exhaustively all possible implementations. It is naturally possible to envisage replacing any of the means described by equivalent means without going beyond the ambit of the present invention.

What is claimed is:

1. A technical maintenance method for a piece of equipment of a vehicle that includes an anti-vibration system, the method comprising the following steps:
   operating the anti-vibration system either in a normal mode of operation in which the anti-vibration system reduces vibrations occurring while the vehicle is operating or in a degraded mode of operation in which the anti-vibration system reduces less or none of the vibrations occurring while the vehicle is operating whereby the equipment is subjected to more of the vibrations occurring while the vehicle is operating when the anti-vibration system is operating in the degraded mode of operation than when the anti-vibration system is operating in the normal mode of operation;
   determining, by a maintenance device in communication with the anti-vibration system, whether the anti-vibration system is operating in the normal mode of operation or in the degraded mode of operation;
   determining, by the maintenance device, a first number (D1) of hours of operation of the equipment while the anti-vibration system was operating in the normal mode of operation;
   determining, by the maintenance device, a second number (D2) of hours of operation of the equipment while the anti-vibration system was operating in the degraded mode of operation;
   converting, by the maintenance device, the second number (D2) of hours of operation into a third number (D3) of hours of operation by applying a predetermined conversion relationship, the third number (D3) of hours of operation acting under normal operating mode conditions to generate damage to the equipment that is equal to the damage caused by the equipment operating during the second number of hours of operation; and
   acting on the equipment when the sum of the first number (D1) plus the third number (D3) reaches a predetermined threshold (D0).

2. The method according to claim 1, wherein the predetermined threshold (DO) is equal to the predetermined lifetime of the equipment.

3. The method according to claim 1, wherein the anti-vibration system operates in the degraded mode of operation when the anti-vibration system has failed, at least in part.

4. The method according to claim 1, wherein the anti-vibration system is an active device.

5. The method according to claim 1, wherein, in order to determine the conversion relationship, the following steps are performed:

estimating the vibratory spectrum of the equipment in use while the anti-vibration system is operating in degraded mode, and deducing a mean vibration level therefrom;

determining an alternative threshold associated with the mean vibration level; and deducing therefrom a conversion relationship corresponding to a multiplicative coefficient equal to the quotient of the predetermined threshold (D0) divided by the alternative threshold.

6. An assembly for maintaining a piece of equipment of a vehicle, the assembly comprising:

an anti-vibration system operating either in a normal mode of operation in which the anti-vibration system reduces vibrations occurring while the vehicle is operating or in a degraded mode of operation in which the anti-vibration system reduces less or none of the vibrations occurring while the vehicle is operating whereby the equipment is subjected to more of the vibrations occurring while the vehicle is operating when the anti-vibration system is operating in the degraded mode of operation than when the anti-vibration system is operating in the normal mode of operation; and a maintenance device for maintaining the equipment, wherein the maintenance device includes a peripheral member and a processor unit communicating with the anti-vibration system, the processor unit being provided with a memory, the processor unit executing instructions stored in the memory in order to:

determine whether the anti-vibration system is operating in a the normal mode of operation or in the degraded mode of operation;

determine a first number of hours of operation of the equipment while the anti-vibration system was operating in the normal mode of operation;

determine a second number of hours of operation of the equipment while the anti-vibration system was operating in the degraded mode of operation;

convert the second number of hours of operation into a third number of hours of operation by applying a predetermined conversion relationship; and signal to an operator the sum of the first number of hours of operation plus the third number of hours of operation.

7. An aircraft and an anti vibration system, the aircraft further comprising:

an anti-vibration system operating either in a normal mode of operation in which the anti-vibration system reduces vibrations occurring while the aircraft is in flight or in a degraded mode of operation in which the anti-vibration system reduces less or none of the vibrations occurring while the aircraft is in flight;

a piece of equipment on board the aircraft, the equipment being subjected to more of the vibrations occurring while the aircraft is in flight when the anti-vibration system is operating in the degraded mode of operation than when the anti-vibration system is operating in the normal mode of operation; and a maintenance device for maintaining the piece of equipment, wherein the maintenance device includes a peripheral member and a processor unit communicating with the anti-vibration system, the processor unit including a memory, the processor unit configured to execute instructions stored in the memory in order to:

determine whether the anti-vibration system is operating in the normal mode of operation or in the degraded mode of operation;

determine a first number of hours of operation of the equipment while the anti-vibration system was operating in the normal mode of operation;

determine a second number of hours of operation of the equipment while the anti-vibration system was operating in the degraded mode of operation;

convert the second number of hours of operation into a third number of hours of operation by applying a predetermined conversion relationship; and signal to an operator the sum of the first number of hours of operation plus the third number of hours of operation.

* * * * *